(12) United States Patent
Ingham et al.

(10) Patent No.: US 11,261,086 B2
(45) Date of Patent: Mar. 1, 2022

(54) PROCESS FOR PRODUCING METHANOL AND AMMONIA

(71) Applicant: Johnson Matthey Davy Technologies Limited, London (GB)

(72) Inventors: Alan Ingham, London (GB); Madhanakrishnan Janardhanan, London (GB); John David Pach, Billingham Cleveland (GB); Kar Chi Yiu, London (GB)

(73) Assignee: Johnson Matthey Davy Technologies Limited, London (GB)

(*) Notice: Subject to any disclaimer, the term of this patent is extended or adjusted under 35 U.S.C. 154(b) by 70 days.

(21) Appl. No.: 16/770,686

(22) PCT Filed: Nov. 29, 2018

(86) PCT No.: PCT/GB2018/053456
§ 371 (c)(1),
(2) Date: Jun. 8, 2020

(87) PCT Pub. No.: WO2019/122809
PCT Pub. Date: Jun. 27, 2019

(65) Prior Publication Data
US 2021/0017023 A1    Jan. 21, 2021

(30) Foreign Application Priority Data
Dec. 18, 2017   (GB) ...................................... 1721126

(51) Int. Cl.
*C07C 273/04*      (2006.01)
*C01B 3/48*        (2006.01)
(Continued)

(52) U.S. Cl.
CPC .................. *C01B 3/48* (2013.01); *B01J 19/24* (2013.01); *C01B 3/025* (2013.01); *C01B 3/382* (2013.01);
(Continued)

(58) Field of Classification Search
None
See application file for complete search history.

(56) References Cited

U.S. PATENT DOCUMENTS

| 4,315,900 A | 2/1982 | Nozawa et al. |
| 4,886,651 A | 12/1989 | Patel et al. |

(Continued)

FOREIGN PATENT DOCUMENTS

| EP | 2 196 448 A1 | 6/2010 |
| EP | 2 805 914 A1 | 11/2014 |

(Continued)

OTHER PUBLICATIONS

Appl, M., "Ammonia, 2. Production Processes In: Ullmann's Encyclopedia of Industrial Chemistry," Wiley-VCH Verlag GmbH & Co. KGaA, first published on Oct. 15, 2011 and presumed same as Nov. 8, 2012 version, DOI: 10.1002/14356007.o02_o11, pp. 175-176.

(Continued)

*Primary Examiner* — Sudhakar Katakam
*Assistant Examiner* — Jennifer C Sawyer
(74) *Attorney, Agent, or Firm* — BakerHostetler

(57) ABSTRACT

A process for the co-production of methanol and ammonia is described comprising the steps of: (a) forming a first synthesis gas stream by reacting a first portion of a hydrocarbon feedstock and steam in a steam reformer, (b) forming a second synthesis gas stream in parallel to the first synthesis gas stream by reacting a second portion of the hydrocarbon feedstock with an oxygen-containing gas and steam in an autothermal reformer, (c) synthesising methanol from a first (Continued)

Figure 1:
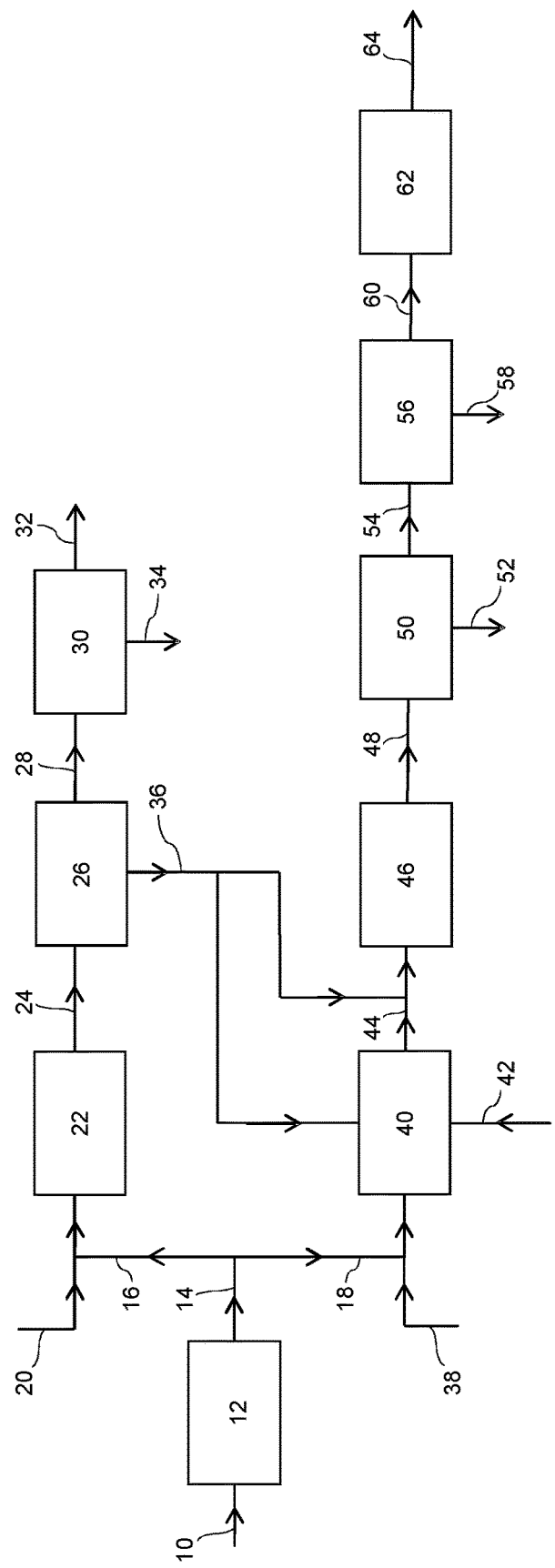

process gas comprising the first synthesis gas stream, and (d) synthesising ammonia from a second process gas prepared from the second synthesis gas stream, wherein a purge stream containing hydrogen is recovered from the methanol synthesis step (c) and a portion of the purge gas stream is fed to the autothermal reformer and/or the second synthesis gas in step (b).

15 Claims, 3 Drawing Sheets

(51) Int. Cl.
*B01J 19/24* (2006.01)
*C01B 3/02* (2006.01)
*C01B 3/38* (2006.01)
*C01C 1/04* (2006.01)
*C07C 273/10* (2006.01)

(52) U.S. Cl.
CPC .......... *C01C 1/0447* (2013.01); *C01C 1/0488* (2013.01); *C07C 273/04* (2013.01); *C07C 273/10* (2013.01); *B01J 2219/0004* (2013.01); *B01J 2219/00038* (2013.01); *C01B 2203/0233* (2013.01); *C01B 2203/0244* (2013.01); *C01B 2203/0283* (2013.01); *C01B 2203/0475* (2013.01); *C01B 2203/061* (2013.01); *C01B 2203/068* (2013.01); *C01B 2203/0833* (2013.01); *C01B 2203/127* (2013.01); *C01B 2203/1241* (2013.01)

(56) References Cited

U.S. PATENT DOCUMENTS

| | | |
|---|---|---|
| 9,981,854 B2 | 5/2018 | Dahl |
| 2010/0150810 A1 | 6/2010 | Yoshida et al. |
| 2016/0083260 A1 | 3/2016 | Dahl |
| 2017/0327383 A1 | 11/2017 | Dahl |
| 2018/0072658 A1 | 3/2018 | Erlandsson et al. |
| 2019/0308919 A1 | 10/2019 | Koss et al. |
| 2020/0087153 A1 | 3/2020 | Han et al. |

FOREIGN PATENT DOCUMENTS

| | | |
|---|---|---|
| EP | 3323786 A | 5/2018 |
| GB | 2 084 973 A | 4/1982 |
| WO | 2014/187621 A1 | 11/2014 |
| WO | 2016/132092 A1 | 8/2016 |
| WO | 2018/166873 A1 | 9/2018 |

OTHER PUBLICATIONS

International Search Report of the International Searching Authority for PCT/GB2018/053456 dated Feb. 11, 2019.
Combined Search and Examination Report of the Intellectual Property Office of the United Kingdom for GB1819436.5 dated May 7, 2019 and search date of May 3, 2019.

PROCESS FOR PRODUCING METHANOL AND AMMONIA

The present invention relates to a process for co-production of methanol and ammonia.

Methanol and ammonia are important chemical intermediates that find widespread use in industry. Processes for ammonia and methanol co-production typically include a step of steam reforming of a hydrocarbon feedstock, such as natural gas, to generate a synthesis gas comprising hydrogen and carbon oxides (carbon monoxide and carbon dioxide) that may be processed into the desired products. Co-production of methanol and ammonia using a combination of steam reforming and autothermal reforming is known. For example, WO2014187621 (A1) discloses a process for co-production of ammonia, urea and methanol from natural gas, comprising the steps of (a) producing a synthesis gas by simultaneous feeding natural gas to an autothermal reformer (ATR) and to a steam methane reformer (SMR), the two reformers running in parallel, (b) feeding air to an air separation unit (ASU), where the air is split into oxygen, which is fed to the ATR, and nitrogen, (c) subjecting the synthesis gas from the SMR to a water gas shift, (d) removing the carbon dioxide from the synthesis gas from step (c) and leading it to urea synthesis in a urea synthesis unit, (e) combining the hydrogen-rich gas from step (d) with the nitrogen from step (b), removing catalyst poisons from the gases and leading the gas mixture to ammonia synthesis in an ammonia synthesis unit, (f) optionally removing part of the carbon dioxide from the syngas from the ATR in step (a) and leading it to urea synthesis in a urea synthesis unit and (g) leading the syngas from step (f) to the methanol synthesis unit, wherein synthesis gas from step (a) may be led either from the ATR outlet to the SMR outlet upstream from the shift stage or the other way.

There is a need to improve the efficiency and cost of building and operating methanol and ammonia co-production processes.

The Applicant has realised that the problems of the prior art processes may be overcome by a combination of using steam reforming to generate a hydrogen-rich synthesis gas for methanol synthesis, autothermal reforming to generate a synthesis gas for ammonia synthesis and using a hydrogen-containing purge stream from the methanol synthesis to adjust the hydrogen content of the synthesis gas for the ammonia synthesis.

Accordingly, the invention provides a process for the co-production of methanol and ammonia comprising the steps of: (a) forming a first synthesis gas stream by reacting a first portion of a hydrocarbon feedstock and steam in a steam reformer, (b) forming a second synthesis gas stream in parallel to the first synthesis gas stream by reacting a second portion of the hydrocarbon feedstock with an oxygen-containing gas and steam in an autothermal reformer, (c) synthesising methanol from a first process gas comprising the first synthesis gas stream, and (d) synthesising ammonia from a second process gas prepared from the second synthesis gas stream, wherein a purge stream containing hydrogen is recovered from the methanol synthesis step (c) and a portion of the purge gas stream is fed to the autothermal reformer and/or the second synthesis gas in step (b).

The invention further provides a system for the co-production of methanol and ammonia comprising (i) a source of a hydrocarbon feedstock, (ii) a steam reformer configured to reform a first portion of the hydrocarbon feedstock and steam to form a first synthesis gas stream, (iii) an autothermal reformer configured to reform a second portion of the hydrocarbon feedstock with an oxygen-containing gas and steam to form a second synthesis gas stream, (iv) a methanol production unit to synthesis methanol from a first process gas comprising the first synthesis gas stream, (v) an ammonia production unit to synthesise ammonia from a second process gas prepared from the second synthesis gas stream, and (vi) a methanol purge gas recovery conduit that provides a portion of a methanol purge gas from the methanol production unit to the autothermal reformer and/or the second synthesis gas stream.

The claimed process makes more efficient use of the methanol purge gas than known processes.

The hydrocarbon feedstock is preferably a methane-rich gas containing >80% by volume methane. Such gases include natural gas, coal bed methane and associated gas, as well as purified biogas. Preferably the hydrocarbon feedstock is natural gas. The natural gas may be supplied to the process at a pressure in the range 10-80 bar abs.

The hydrocarbon feedstock may if required be desulphurised upstream of the steam reformer and autothermal reformer. Preferably the hydrocarbon feedstock is desulphurised and then divided into the first portion and the second portion. Preferably a single desulphurisation unit is used. The desulphurisation unit may comprise a bed of hydrodesulphurisation (HDS) catalyst followed by one or more beds of hydrogen sulphide adsorbent. Suitable HDS catalysts are commercially available and typically comprise supported cobalt or nickel molybdate or tungstate catalysts, or nickel and copper-promoted zinc oxide catalysts. Suitable hydrogen sulphide adsorbents are commercially available and typically comprise zinc oxide. For hydrodesulphurisation, a small amount of a hydrogen-containing gas is added to the hydrocarbon feedstock. The hydrogen-containing gas may be any suitable hydrogen-containing gas having sufficient hydrogen to support the HDS reactions, but in the present process may suitably be a portion of the hydrogen-rich gas stream. Suitable operating conditions for the HDS catalyst and hydrogen sulphide adsorbents are temperatures in the range 250 to 400° C. and pressures in the range 30 to 80 bar abs, with the hydrogen content of the feed gas for the HDS catalyst suitably in the range 2-5% by volume.

The hydrocarbon feedstock, preferably after any desulphurisation, is divided using any suitable means into a first portion and a second portion. The first portion is reacted with steam in a steam reformer to form the first synthesis gas stream. The second portion is reacted with an oxygen-containing gas in an autothermal reformer to form the second synthesis gas stream in parallel. The portions fed to the steam reformer and autothermal reformer may be the same, i.e. 50:50 or different, depending on the desired output of the process. In a preferred process, more hydrocarbon feedstock is sent to the steam reformer than the autothermal reformer, for example 60% by volume, preferably 75% by volume, more preferably 80% by volume of the hydrocarbon feedstock is sent to the steam reformer. The ammonia production is satisfactory because the methanol purge gas stream provides hydrogen for the ammonia synthesis If the hydrocarbon feedstock contains higher hydrocarbons than methane, such as ethane, propane, butane and longer chain hydrocarbons, it may, before being subjected to steam reforming and/or autothermal reforming, be subjected to a step of pre-reforming in order to convert the higher hydrocarbons to methane. This reduces the risk of carbon formation in the tubes of the steam reformer and may allow a lower overall steam-to-carbon ratio to be employed, which in turn improves process efficiency and/or throughput. Pre-reforming may be carried out by passing the hydrocarbon feedstock, preferably after any step of desulphurisation, and steam adiabatically through a bed of steam reforming catalyst. In adiabatic pre-reforming, a mixture of hydrocarbon and steam, typically at a steam to carbon ratio in the range 1-4, is passed at an inlet temperature in the range 300-620° C. and a pressure in the range 10 to 80 bar abs to a fixed bed of pelleted nickel-containing pre-reforming catalyst. Such catalysts are commercially available and typically comprise ≥40% wt nickel (expressed as NiO) and may be prepared by co-precipitation of a nickel-containing material with alumina and promoter compounds such as silica and magnesia.

The feed streams for the steam reformer and the autothermal reformer, and the desulphurisation unit and pre-reformer if present, may be preheated by heat exchange with any hot gas, such as a boiler flue gas or in a fired heater. However, in the present invention, it is preferred that one or more process streams selected from the hydrocarbon feedstock, the first and/or second portions of the hydrocarbon feedstock, steam and the oxygen-containing gas are pre-heated in a flue gas duct of the steam reformer. In a preferred arrangement, the second portion of hydrocarbon and the oxygen-containing gas fed to the autothermal reformer are pre-heated in a flue gas duct of the steam reformer, which removes the need for a separate fired heater.

In the steam reformer, the first portion of hydrocarbon feedstock is reformed with steam in externally-heated catalyst-filled tubes in a fired-steam reformer. The steam may be combined with the hydrocarbon feedstock by direct addition of steam or may be added by passing the hydrocarbon through a saturator fed with water. The steam to carbon ratio, being the molar ratio of steam to hydrocarbon carbon present in the feed, is typically in the range 2 to 5. The steam reforming catalyst typically comprises nickel at levels in the range 5-30% wt, supported on shaped refractory oxides, such as alpha alumina, magnesium aluminate or calcium aluminate. If desired, catalysts with different nickel contents may be used in different parts of the tubes, for example catalysts with nickel contents in the range 5-15% wt or 30-85% wt may be used advantageously at inlet or exit portions of the tubes. Alternatively, structured catalysts, wherein a nickel or precious metal catalyst is provided as a coated layer on a formed metal or ceramic structure may be used, or the catalysts may be provided in a plurality of containers disposed within the tubes. Steam reforming reactions take place in the tubes over the steam reforming catalyst at temperatures above 350° C. and typically the process fluid exiting the tubes is at a temperature in the range 650-950° C. The combustion gas heat exchange medium flowing around the outside of the tubes may have a temperature in the range 800-1300° C. The pressure may be in the range 10-80 bar abs. Such steam reforming apparatus and catalysts are commercially available.

In the autothermal reformer, the second portion of the hydrocarbon feedstock is partially combusted using an oxygen-containing gas often in a burner apparatus mounted usually near the top of the reformer. The oxygen to carbon ratio inlet the autothermal reformer may be in the range 0.5:1 to 1.5:1 (O:C). Steam is also fed to the autothermal reformer and may be included with the hydrocarbon feed or oxygen containing gas. The amount of steam may be such that the steam to carbon ratio is in the range 0.5-5. The partially combusted gas is then passed adiabatically through a bed of a steam reforming catalyst usually disposed below the burner apparatus, to bring the gas composition towards equilibrium. Heat for the endothermic steam reforming reaction is supplied by the hot, partially combusted gas. As the partially combusted gas contacts the steam reforming catalyst it is cooled by the endothermic steam reforming reaction to temperatures in the range 800-1100° C. The bed of steam reforming catalyst in the autothermal reformer typically comprises nickel at levels in the range 5-30% wt, supported on shaped refractory oxides, but layered beds may be used wherein the uppermost catalyst layer comprises nickel or a precious metal, such as platinum or rhodium, on a zirconia support. Such autothermal reforming apparatus and catalysts are commercially available.

As for the steam reformer, the operating pressure of the autothermal reformer may be in the range 10-80 bar abs, but because the process is operated in parallel it may alternatively be operated at 80-200 bar abs. This has the advantage that the compression of the second process gas for the ammonia synthesis step may be simplified and reduced in cost.

The oxygen-containing gas used in the autothermal reformer may be a pure oxygen stream containing, for example 90% by volume $O_2$, but is preferably selected from air or an oxygen-enriched air. If pure oxygen is used, then nitrogen for ammonia synthesis will need to be added to the second synthesis gas before or preferably after the stages of water gas shift, carbon dioxide removal and methanation, so that it is present in the second process gas at the required $H_2:N_2$ ratio of about 3:1 before the ammonia synthesis. The nitrogen may be provided by known means such as an air separation unit. Using air is particularly preferred in the present process because it avoids the need for an air separation unit.

The steam reformer provides the first synthesis gas stream. This synthesis gas stream comprises hydrogen, carbon dioxide, carbon monoxide and unreacted methane and steam. The hydrogen content of the first synthesis gas stream, before any treatment to form the first process gas, may be in the range 50 to 80% by volume on a dry gas basis. Before methanol synthesis, the first synthesis gas is subjected to cooling to below the dew point to condense the steam, which may be separated using conventional gas-liquid separators. The cooling may be provided using one or more heat exchangers fed with a suitable coolant, e.g. with cooling water. The condensate recovered may be fed to a condensate stripping unit or, if desired, be fed to steam generators that produce steam for the synthesis gas generation and/or water-gas shift stages. The cooled synthesis gas may if desired be subjected to further purification, e.g. using a scrubber fed with water, and/or a guard bed of a suitable adsorbent material in a guard vessel. The resulting de-watered first synthesis gas forms part of the first process gas fed to the methanol production unit.

The methanol is synthesised in a methanol production unit by steps comprising passing the first process gas through a bed of methanol synthesis catalyst disposed in a methanol synthesis reactor to form a methanol-containing product gas, recovering methanol and an unreacted gas stream from the methanol-containing product gas, returning a portion of the unreacted gas stream to the methanol synthesis reactor in a synthesis loop and recovering the purge stream containing hydrogen from the synthesis loop.

Methanol is synthesised from the first process gas. The synthesis reactions may be depicted as follows:

$$3H_2 + CO_2 \rightleftharpoons CH_3OH + H_2O$$

$$2H_2 + CO \rightleftharpoons CH_3OH$$

The first process gas is preferably heated to a suitable methanol synthesis inlet temperature and fed to the methanol production unit. The methanol production unit comprises a methanol synthesis reactor containing a methanol synthesis catalyst. The process is operated in a synthesis loop such that unreacted product gas recovered from the methanol synthesis reactor, after methanol removal, is compressed to the first synthesis gas pressure, mixed with the de-watered first synthesis gas in the desired ratio to form the first process gas which is fed to the methanol synthesis reactor. The first process gas may be heated using one or more heat exchangers, for example a gas-gas interchanger that recovers heat from a product gas stream recovered from the methanol synthesis reactor.

The methanol synthesis, because it is exothermic, may involve cooling the catalyst and reacting gases by indirect heat exchange surfaces in contact with the reacting gas, or by subdividing the catalyst bed and cooling the gas between the beds by injection of cooler gas or by indirect heat exchange. Accordingly, the methanol synthesis reactor may be selected from a gas-cooled converter, a tube-cooled converter, and axial steam-raising converter, a radial steam-raising converter and a quench reactor. Any methanol synthesis catalyst may be used, but preferably it is based on a promoted or un-promoted copper/zinc oxide/alumina composition, for example those having a copper content in the range 50-70% wt, preferably 50-60% wt. Promoters include oxides of Mg, Cr, Mn, V, Ti, Zr, Ta, Mo, W, Si and rare earths. In the catalyst, the zinc oxide content may be in the range 20-90% wt, preferably 20-40% wt. The proportion of aluminium oxide in the catalyst is preferably in the range 5-15% wt. The one or more oxidic promoter compounds, if present, may be present in an amount in the range 0.01-10% wt. Magnesium compounds are preferred promoters and the catalyst preferably contains magnesium in an amount 1-5% wt, expressed as MgO. Such methanol production apparatus and catalysts are commercially available.

The first process gas may be passed over the catalyst at an inlet temperature to the catalyst in the range 200-320° C., and at a pressure in the range 20-250 bar abs, preferably 20-120 bar abs, and a space velocity in the range 500-20000 $h^{-1}$. Preferably the methanol synthesis step is operated at a pressure equal or greater than the operating pressure of the autothermal reformer as this removes the need to compress the purge gas stream.

A crude methanol product comprising methanol, water and trace amounts of impurities such as ethanol is separated from unreacted gas in the product gas stream recovered from the methanol synthesis reactor. The crude methanol may be recovered by cooling of the product gas stream recovered from the methanol synthesis reactor to below the dew point, e.g. with cooling water. If desired, liquid ammonia may be used in a further cooling stage. The gas-liquid mixture may be fed to a conventional gas-liquid separator to separate the crude methanol from the unreacted gas. Alternatively, or in addition, methanol may be recovered by scrubbing the product gas with water.

In the present process, a single stage of methanol synthesis is sufficient. Nevertheless, if desired, the methanol synthesis may be part of a multiple stage process where the product gas, with or without condensate removal, is fed to one or more further methanol synthesis reactors operating in series or in parallel, which may contain the same or different methanol synthesis catalysts.

The purge gas stream is removed from the unreacted gas to prevent the undesirable build-up of inert/unreactive gases in the methanol synthesis loop. The proportion of the unreacted gas recovered as the purge gas stream may vary depending on a variety of factors such as the hydrocarbon feedstock composition, the methane slip from reformer, the operating pressure and temperature and the number of recycles in the methanol synthesis loop. The amount of purge gas may be in the range 1-60% by volume, preferably 1-20%, more preferably 1-10% by volume of the unreacted gas following methanol recovery. The purge gas stream is preferably removed downstream of methanol recovery and upstream of compression of the recirculating unreacted gas. By using a steam reformer to produce the first synthesis gas, the hydrogen to carbon ratio in the first synthesis gas is greater than the theoretical amount required for methanol synthesis and so the loop gas, and consequently the purge gas stream, contains an excess of hydrogen. This hydrogen is used to supplement the hydrogen in the second process gas used to produce the ammonia.

A portion of the purge gas is recovered for use in the ammonia synthesis. The purge gas may be added directly to the autothermal reformer or may conveniently be mixed with the second portion of the hydrocarbon feed, before or after any steam addition. The proportion of the purge gas stream fed to the autothermal reformer or second synthesis gas may be in the range 50 to 100% by volume, preferably 90 to 100% by volume, more preferably all of the purge gas recovered from the loop. The remaining portion of the purge gas, if any, may be used as a fuel gas or as a source of hydrogen for the hydrodesulphurisation. The entire amount of the portion of the purge gas may be fed to the autothermal reformer, or the entire amount may be fed to the second synthesis gas. Alternatively, the portion of the purge gas may be divided between the autothermal reformer and the second synthesis gas.

Feeding the purge gas to the autothermal reformer and/or second synthesis gas allows the autothermal reformer to be operated efficiently with air as the oxygen-containing gas which removes the need for an air separation unit. It also removes the need for adjustment of the hydrogen:nitrogen ratio in the second feed gas upstream of the ammonia synthesis. This simplification of the ammonia process offers considerable savings in capital and operating costs.

The purge stream may contain 50-90% by volume of hydrogen and other gases including carbon monoxide, carbon dioxide and methane. A portion of the purge stream is fed to the autothermal reformer or the second synthesis gas upstream of a water-gas shift stage. By feeding the portion of the purge gas upstream of the water-gas shift stage, the carbon monoxide may be used to make more hydrogen before removing all the carbon oxides in downstream carbon dioxide removal and methanation units. If the portion of the purge gas was fed downstream of the water-gas shift stage this benefit would not be obtained and more hydrogen would be consumed on the methanator to form methane, which adds to the total inert level in the ammonia synthesis.

Whereas the purge gas stream containing hydrogen may be fed directly to the autothermal reformer and/or second synthesis gas, it may be desirable to use a hydrogen-rich gas formed by separating off at least a portion of the other components. Thus, in some embodiments the purge gas stream containing hydrogen may be separated into a hydrogen-rich gas stream and a hydrogen-depleted gas stream. To avoid consuming hydrogen in the autothermal reformer it is desirable to feed the hydrogen-rich gas to the second synthesis gas. The hydrogen-rich gas stream may be obtained using any known hydrogen-separation equipment, such as hydrogen membrane separators. These are preferably used to generate the hydrogen-rich gas from a washed or scrubbed purge gas stream and are preferred over other hydrogen separation techniques such as pressure swing absorption because the operating pressure of the membrane separator allows the hydrogen-rich gas and the hydrogen depleted gas to be used without additional compression. The hydrogen-rich gas desirably comprises ≥85% by volume of $H_2$.

An advantage of using the hydrogen-rich gas instead of the purge gas directly is that it minimises the amount of inert gases going forward to the ammonia loop.

The hydrogen-depleted gas will typically contain carbon oxides and methane and potentially some hydrogen. Whereas it may be used as a fuel and combusted to produce heat in the steam reformer, it is most preferably fed to the autothermal reformer to form part of the second synthesis gas. In this way, the methane in the purge gas will be reformed to maximise the hydrogen production for the ammonia synthesis. It is also a useful source of carbon dioxide that may be used to generate urea from the ammonia. The hydrogen-depleted gas may be added directly to the autothermal reformer or may conveniently be mixed with the second portion of the hydrocarbon feed, before or after any steam addition.

The crude methanol stream recovered from the methanol production unit contains water and other impurities. The crude methanol may be sent for storage in a suitable storage tank. Alternatively, the crude methanol may be subjected to one or more purification stages, including a de-gassing stage and/or one or more stages of distillation in a methanol purification unit. The de-gassing stage and/or any distillation stages may be provided by distillation columns heated using heat recovered from the process.

In the present process, preferably at least a portion of the crude methanol is purified by distillation.

If desired, at least a portion of the methanol may be reacted with air over an oxidation catalyst in a formaldehyde production unit to form formaldehyde. The formaldehyde may be used to produce a formaldehyde stabiliser such as an aqueous urea formaldehyde concentrate (UFC) or aqueous formaldehyde (formalin). Urea formaldehyde concentrate that may be used typically comprises a mixture of about 60% wt formaldehyde, about 25% wt urea and the balance about 15% water. Such a product may be termed "UFC85". Other UFC products may also be used, e.g. UFC80. Other formaldehyde products may also be produced. Excess formaldehyde products may be recovered and sold.

The formaldehyde stabiliser production unit may comprise an oxidation reactor containing an oxidation catalyst as a fixed bed or within externally-cooled tubes disposed within the reactor. The oxidation catalyst may be selected from either a silver catalyst or a metal oxide catalyst, preferably comprising a mixture of iron and molybdenum oxides. Vanadium oxide catalysts may also be used. The catalyst is preferably a mixture of iron molybdate $Fe_2(MoO_4)_3$ and molybdenum trioxide $MoO_3$ with a Mo:Fe atomic ratio between 2 and 3. The inlet temperature to the oxidation reactor is typically in the range 80-270° C., with iron-based catalytic processes operating up to 400° C. and silver-based processes up to 650° C. An absorption tower may be used to extract the formaldehyde product from the oxidised gas mixture into either water to produce aqueous formaldehyde solution, or a urea solution to produce a urea-formaldehyde concentrate (UFC). The absorption tower may contain a selection of packing, trays and other features to promote the absorption, and cooling water may be used to provide the product at a temperature in the range 20-100° C. The absorption stage typically runs at a slightly lower pressure than the oxidation reactor.

The formaldehyde production unit may use purified methanol as the feed or a crude methanol as the feed. By "crude methanol" we include the direct product of the methanol synthesis reactor and a methanol product in which the water content has been adjusted to the range 5-20% by weight so that the formaldehyde stabiliser products are produced efficiently at suitable concentrations. This makes it possible to send crude methanol directly to the formaldehyde production unit without the need for multiple distillation steps. Using crude methanol saves both capital cost on distillation columns and associated equipment, as well as the operating cost of this equipment, resulting in a significant benefit.

The autothermal reformer produces the second synthesis gas stream. The second synthesis gas stream contains hydrogen, carbon monoxide, carbon dioxide, steam and methane and may contain nitrogen if air or oxygen-enriched air are fed to the autothermal reformer. The hydrogen content of the second synthesis gas may be in the range 25 to 70% by volume on a dry gas basis depending on how much hydrogen is in the feed and whether air or oxygen are used. The second process gas fed to the ammonia synthesis stage preferably consists essentially of hydrogen and nitrogen and therefore the second synthesis gas is subjected to further processing stages to form the second process gas. Preferably the second process gas is prepared by steps comprising passing the second synthesis gas through one or more stages of water-gas shift to form a shifted gas stream, separating carbon dioxide from the shifted gas stream in a carbon dioxide removal unit, and converting any remaining carbon oxides present in the second process stream to methane in a methanation unit downstream of the carbon dioxide removal unit.

The hydrogen content of the second synthesis gas may be further increased by subjecting it, optionally following steam addition, to one or more stages of water gas shift to produce a shifted synthesis gas stream with the desired gas composition. In a water-gas shift stage, a portion of the carbon monoxide is converted to carbon dioxide and the hydrogen content is increased. Any suitable catalytic shift conversion reactor and catalyst may be used. If insufficient steam is present, steam may be added to the gas stream before it is subjected to the water-gas shift conversion. The reaction may be depicted as follows;

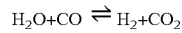

$$H_2O + CO \rightleftharpoons H_2 + CO_2$$

The reaction may be carried out in one or more stages. The, or each, stage may be the same or different and may be selected from high temperature shift, low temperature shift, medium temperature shift, isothermal shift and sour shift, and is preferably selected from a single stage of high temperature shift, a combination of high temperature shift and low temperature shift, a single stage of medium temperature shift, or a combination of medium temperature shift and low temperature shift.

High temperature shift catalysts may be promoted iron catalysts such as chromia- or alumina-promoted magnetite catalysts. Other high temperature shift catalysts may be used, for example iron/copper/zinc oxide/alumina catalysts, manganese/zinc oxide catalysts or zinc oxide/alumina catalysts. Medium, low temperature and isothermal shift catalysts typically comprise copper, and useful catalysts may comprise varying amounts of copper, zinc oxide and alumina. Such water-gas shift apparatus and catalysts are commercially available.

For high temperature shift catalysts, the temperature in the shift converter may be in the range 300-460° C., for medium temperature shift catalysts the temperature may be in the range 190-350° C. and for low-temperature shift catalysts the temperature may be 185-270° C. The flow-rate of synthesis gas containing steam may be such that the gas hourly space velocity (GHSV) through the bed of water-gas shift catalyst in the reactor may be ≥6000 hour$^1$. The pressure may be in the range 10-200 bar abs.

The water-gas shift stage produces a shifted gas. By the term shifted gas we include a partially shifted gas in which the conversion of carbon monoxide to carbon dioxide is incomplete.

In a preferred embodiment, the water-gas shift stage comprises a high temperature shift stage or a medium temperature shift stage or an isothermal shift stage with or without a low temperature shift stage. In a particularly preferred arrangement, the water-gas shift stage comprises a high temperature shift stage to form a partially shifted gas and, following adjustment of the temperature of the partially shifted gas, a low temperature shift stage to form a shifted gas mixture.

Steam present in the shifted gas mixture may be condensed to form a dried shifted gas. This may be achieved by cooling the shifted gas to below the dew point using one or more heat exchangers fed, for example, with cooling water. The condensate recovered may be fed to a condensate stripping unit or, if desired, be fed to steam generators that produce steam for the synthesis gas generation and/or water-gas shift stages.

The shifted gas or the dried shifted gas may be fed to a carbon dioxide removal unit. The carbon dioxide removal unit may be located downstream of a water-gas shift stage, and upstream of the methanation stage. Any suitable carbon dioxide removal unit may be used. Suitable removal units may function by reactive or chemical absorption, such as those known as aMDEA® or Benfield® units that are based on using regenerable amine or potassium carbonate washes, or by physical absorption, based on using methanol, glycol or another liquid at low temperature, such as Rectisol®, Selexol® units. Carbon dioxide removal may also be performed by means of pressure-swing adsorption (PSA) using suitable solid adsorbent materials. PSA may also be used to adjust the nitrogen content if desired. Such carbon dioxide removal apparatus and materials are commercially available. Some or all of the carbon dioxide formed in the synthesis gas may be removed to produce a gas stream comprising mainly hydrogen and nitrogen with low levels of carbon monoxide and/or carbon dioxide. The carbon dioxide removed by the carbon dioxide removal unit may be captured, optionally treated to remove contaminants such as hydrogen, and stored or used for reaction downstream with the ammonia produced to form urea.

In the methanation stage, residual carbon monoxide and any carbon dioxide in the carbon dioxide depleted synthesis gas is converted to methane in a methanator in the methanation unit. A methanator, or methanation reaction vessel, typically contains a bed on methanation catalyst. Any suitable arrangement for the methanator may be used. Thus, the methanator may be operated adiabatically or isothermally. One or more methanators may be used in series or in parallel. A nickel-based methanation catalyst may be used. For example, in a single methanation stage, the gas from the carbon dioxide removal unit may be fed at an inlet temperature in the range 200-400° C., preferably 250-325° C., to a fixed bed of pelleted nickel-containing methanation catalyst. Such catalysts are typically pelleted compositions, comprising 20-40% wt nickel. The pressure for methanation may be in the range 10-80 bar abs or higher up to 250 bar abs. Such methanation apparatus and catalysts are commercially available.

Steam is present in the carbon dioxide-depleted gas recovered from the carbon dioxide removal unit and is formed as a by-product of methanation. The steam is desirably removed in the methanation unit by cooling the methanated gas recovered from the methanator, e.g. by heat exchange with cold water, and separation of condensate to form a de-watered methanated gas stream. The condensate recovered may be fed to a condensate stripping unit or, if desired, be fed to steam generators that produce steam for the synthesis gas generation and/or water-gas shift stages. In addition, or alternatively, conventional syngas driers or ammonia washing may be used to remove the water from the methanated gas.

If necessary, the hydrogen:nitrogen molar ratio of the de-watered methanated gas stream may be adjusted, for example by addition of nitrogen from a suitable source, or by removal of nitrogen, to provide the ammonia synthesis gas. The adjustment of the hydrogen:nitrogen molar ratio is desired to ensure the ammonia synthesis reaction operates efficiently. Nitrogen, if added, may be provided from any source, for example from an air separation unit (ASU) and the adjustment may be performed by direct addition of nitrogen to the de-watered methanated gas stream. Nitrogen, if removed, may be removed from the synthesis gas by cryogenic cooling to recover liquid nitrogen or may be achieved using pressure-swing adsorption on a suitable adsorbent. Cryogenic purification may also be used to remove methane to reduce the amount of inerts fed to the ammonia synthesis loop. Such cryogenic and pressure-swing absorption apparatus and adsorbents are commercially available. The adjusted gas mixture may then be passed to the ammonia production unit.

Preferably, the ammonia is synthesised in an ammonia production unit by passing the second process gas through a bed of ammonia synthesis catalyst disposed in an ammonia synthesis reactor to form an ammonia-containing product gas, recovering ammonia and an unreacted gas stream from the ammonia-containing product gas, returning a portion of the unreacted gas stream to the ammonia synthesis reactor in a synthesis loop and recovering a purge stream containing methane from the synthesis loop.

The second process gas may be compressed to the ammonia synthesis pressure and passed to an ammonia production unit. The ammonia production unit comprises an ammonia converter containing an ammonia synthesis catalyst. The converter may be operated adiabatically or the catalyst and/or reacted gases may be cooled. One or more beds of catalyst may be used in the converter with optional cooling of the reacted gases between beds. One or more converters may be used in parallel if required. The nitrogen and hydrogen react together over the catalyst to form the ammonia product according to the following equation:

$$N_2 + 3H_2 \rightleftharpoons 2NH_3$$

Ammonia synthesis catalysts are typically iron based but other ammonia synthesis catalysts may be used. The reactor may operate adiabatically or may be operated isothermally. The catalyst beds may be axial and/or radial flow and one or more beds may be provided within a single converter vessel. The conversion over the catalyst is generally incomplete and so the synthesis gas is passed to a loop containing a partially reacted gas mixture recovered from the ammonia converter and the resulting mixture fed to the catalyst. In the ammonia production unit, the hydrogen/nitrogen mixture may be passed over the ammonia synthesis catalyst at high pressure, e.g. in the range 80-350 bar abs, preferably 150-350 bar abs for large-scale plants, and a temperature in the range 300-540° C., preferably 350-520° C.

A purge gas stream containing methane and hydrogen may be taken from the ammonia synthesis loop, and fed as a fuel to the steam reformer. Optionally hydrogen may be recovered from this ammonia purge stream and used in the process.

Compression, if required, of the second process gas is preferably effected in multiple stages, for example with a first and second stages performed before methanation to achieve a pressure of e.g. 50-100 barg, preferably 80-100 barg, and a third stage before or after methanation to achieve a higher pressure, e.g. 150-250 barg, before the ammonia synthesis.

If desired, at least a portion of the ammonia may be reacted with carbon dioxide in a urea production unit to from urea. Typically, only a portion of the ammonia produced will be used to produce urea, which is limited by the amount of carbon dioxide recovered by the carbon dioxide removal unit. In a preferred embodiment, at least a portion of the carbon dioxide used for urea production is recovered from the purge gas stream recovered from the methanol loop. The excess ammonia may be recovered and sold and/or used to make nitric acid and ammonium nitrate. Any urea production technology may be used. If desired, a stabilised urea may be produced by mixing urea and a stabiliser prepared using formaldehyde recovered from a formaldehyde stabiliser production unit. The stabiliser may be any formaldehyde-containing stabiliser; including aqueous formaldehyde and an aqueous urea-formaldehyde concentrate (UFC). Aqueous formaldehyde and urea formaldehyde concentrate may be prepared directly in the formaldehyde stabiliser production unit. Formaldehyde, either as a concentrated solution or as a combined solution of urea and formaldehyde may be added to molten urea prior to forming into either prills or granules. This reduces the tendency of the urea to absorb moisture and increases the hardness of the surface of the solid particles, preventing both caking (bonding of adjacent particles) and dusting (abrasion of adjacent particles). This maintains the free flowing nature of the product; prevents loss of material through dust, and enhances the stability during long term storage. If urea is available then it is preferable to use the urea formaldehyde solution as a stable solution with a higher formaldehyde concentration can be produced, which minimises the water being added to the molten urea. Accordingly, in one embodiment at least a portion of the ammonia is reacted with carbon dioxide in a urea production unit to from urea, at least a portion of the formaldehyde is reacted with the urea to form a urea-formaldehyde concentrate, and at least a portion of the urea-formaldehyde concentrate is reacted with urea to form a stabilised urea product. Such stabilised urea production apparatus is commercially available.

Figure 2:
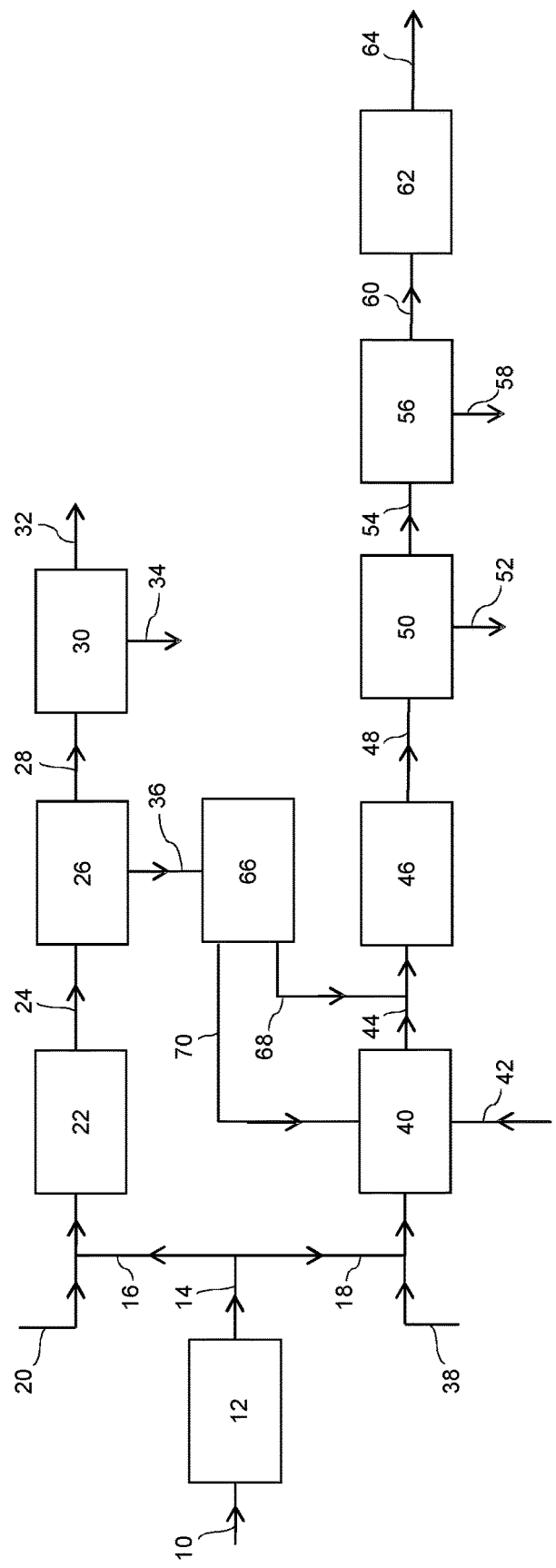
Figure 3:
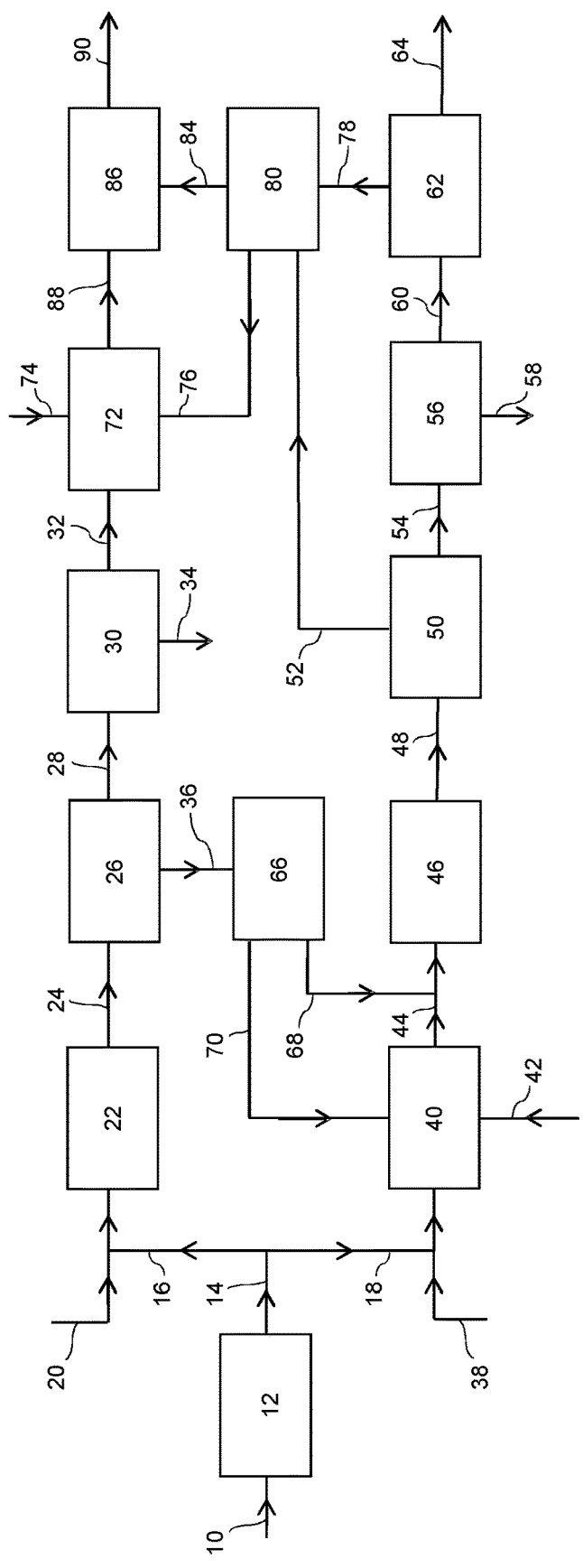

The invention will now be described by reference to the accompanying drawings in which;

FIG. 1 is a schematic representation of a process according to one aspect of the present invention utilizing an untreated methanol purge gas, FIG. 2 is a schematic representation of a process according to a further aspect of the present invention utilizing a hydrogen-rich gas separated from a methanol purge gas, and FIG. 3 is a schematic representation of a process according to a further aspect of the present invention in which the process is integrated with urea and formaldehyde production units.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

In FIG. 1, a natural gas stream 10 is fed to a desulphurisation unit 12 where it is mixed with 2-5% vol. hydrogen and passed over a hydrodesulphurisation catalyst and then a bed of hydrogen sulphide adsorbent. The desulphurised natural gas stream 14 is divided to form a first portion 16 and a second portion 18. The first portion 16 is combined with steam fed via line 20 and the resulting mixture fed to a fired steam reformer 22 where it is steam reformed in externally-heated catalyst-filled tubes to generate a first synthesis gas stream. The first synthesis gas stream recovered from the steam reformer 22 is cooled to below the dew point by one or more stages of heat exchange and the resulting condensate separated by a gas-liquid separator (not shown).

The de-watered synthesis gas is then fed via line 24 to a methanol production unit 26 where it is combined with a portion of a methanol loop gas to form the first process gas, heated and fed to a methanol synthesis reactor containing a bed of methanol synthesis catalyst.

Methanol is synthesised over the catalyst and the product gas from the reactor is cooled to below the dew point in one or more stages of heat exchange to condense methanol from the unreacted gas stream. Crude methanol is recovered using a gas liquid separator (not shown) and fed via line 28 to a purification unit 30 where it is subjected to one or more stages of distillation to produce a purified methanol product 32. A water by-product stream is recovered from the purification unit 30 via line 34. The unreacted gas stream recovered from the gas-liquid separator is compressed and returned to the methanol synthesis reactor as the loop gas. Prior to compression, a portion of the unreacted gas is recovered from the methanol production unit 26 as a purge gas stream 36.

The second portion of desulphurised natural gas 18 is combined with steam fed via line 38 and the resulting mixture fed to an autothermal reformer 40 where it is partially combusted with air fed via line 42 and the partially combusted gas subjected to steam reforming in a bed of steam reforming catalyst in the autothermal reformer downstream of the burner. The resulting second synthesis gas stream is cooled and fed via line 44 to one or more stages of water gas shift in a water gas shift unit 46, where the hydrogen content of the second synthesis gas is increased and the carbon monoxide converted to carbon dioxide by reaction with steam over one or more beds of water-gas shift catalyst.

In this embodiment, the purge gas stream is fed without treatment via line 36 to the autothermal reformer 40 and/or the second synthesis gas stream 44. The purge gas may be added directly to the autothermal reformer 40 or may be mixed with the second portion of desulphurised natural gas 18, or the mixture of the second portion of desulphurised natural gas 18 and steam 38.

A shifted gas is recovered from the water-gas shift unit 46, cooled and fed via line 48 to a carbon dioxide removal unit 50 where it is subjected to carbon dioxide removal using a chemical or physical absorbent liquid. The carbon dioxide removal unit also removes residual water from the shifted gas. The carbon dioxide is separated from the absorbent liquid and recovered via line 52.

A carbon dioxide-depleted gas is recovered from the carbon dioxide removal unit 50, heated and fed via line 54 to a methanation unit 56 comprising a methanator containing a bed of methanation catalyst. Residual carbon oxides in the carbon-dioxide-depleted gas are methanated to form methane. The methanated gas stream is cooled to below the dew point by one or more stages of heat exchange and the resulting condensate separated by a gas-liquid separator (not shown). The condensate is recovered from the methanation unit via line 58.

A de-watered methanated gas recovered from the methanation unit 56 is compressed, heated and fed via line 60 to an ammonia production unit 62 comprising an ammonia synthesis reactor containing a bed of ammonia synthesis catalyst, where it is mixed with an ammonia loop gas to form the second process gas. The second process gas is passed over the ammonia synthesis catalyst. Ammonia is synthesised. The product gas from the ammonia synthesis reactor is cooled to below the dew point in one or more stages of heat exchange to condense ammonia from the unreacted gas stream which is recirculated to the ammonia synthesis reactor. The condensed ammonia is recovered using a gas liquid separator (not shown) to provide a purified ammonia product 64.

In FIG. 2, the process is the same as that depicted in FIG. 1 except the purge gas stream 36 is fed to a hydrogen separation unit 66 where it is washed with water in a scrubbing unit and passed over a hydrogen separation membrane in a membrane separator to generate a hydrogen-rich gas stream 68 and a hydrogen-depleted gas stream 70. The hydrogen-rich gas stream 68 is fed to the second synthesis gas stream 44 where it supplements the hydrogen content of the gas fed to the water-gas shift stage 46. The hydrogen-depleted gas steam, which comprises carbon oxides and methane, is fed via line 70 to the autothermal reformer 40. The hydrogen-depleted gas may be added directly the autothermal reformer 40 or may be mixed with the second portion of desulphurised natural gas 18, or the mixture of the second portion of desulphurised natural gas 18 and steam 38.

In FIG. 3, the process is the same as that depicted in FIG. 2 except a portion of the crude methanol stream 28 or, as depicted, a portion of the purified methanol product 32, is fed to a formaldehyde stabiliser production unit 72 where it is oxidised with air fed via line 74 and the formaldehyde absorbed using an aqueous urea stream fed via line 76 to form a urea-formaldehyde concentrate (UFC). In addition, a portion of the purified ammonia product from the ammonia production unit 62 is fed via line 78 to a urea production unit 80 where it is reacted with the carbon dioxide stream 52 recovered from the carbon dioxide separation unit 50 to form a urea product. The urea product is fed via line 84 to a urea stabilisation unit 86 where it is reacted with the UFC fed via line 88 from the formaldehyde stabiliser production unit 72. The resulting UFC-stabilised urea is recovered from the stabilisation unit 86 via line 90.

The present invention will now be further described by reference to the following Example.

A process according to FIG. 2 was modelled using conventional modelling software on a 11330 kmol/h natural gas feed and produces 6325 mt/day methanol and 4164 mt/day ammonia using an air-fed autothermal reformer without an air separation unit.

The compositions, temperatures and pressures for the streams are set out in the following tables.

| Stream | 10 | 14 | 16 | 18 | 20 | 24 | 28 | 36 |
|---|---|---|---|---|---|---|---|---|
| Pressure (bara) | 30.0 | 29.0 | 29.0 | 29.0 | 30.0 | 24.0 | 78.0 | 78.0 |
| Temp (° C.) | 30 | 250 | 250 | 250 | 250 | 880 | 40 | 40 |
| Flow (kmol/h) | 11330 | 11601 | 10239 | 1362 | 28087 | 55733 | 10979 | 11290 |
| Mole fraction (%) | | | | | | | | |
| Water | | 0.00 | 0.00 | 0.00 | 100.00 | 30.01 | 23.60 | 0.05 |
| Hydrogen | | 1.95 | 1.95 | 1.95 | | 51.64 | 0.29 | 83.70 |
| Carbon Monoxide | | 0.05 | 0.05 | 0.05 | | 10.86 | 0.05 | 2.33 |
| Carbon Dioxide | 1.40 | 1.41 | 1.41 | 1.41 | | 5.03 | 0.55 | 2.00 |
| Methane | 96.81 | 94.81 | 94.81 | 94.81 | | 2.43 | 0.51 | 11.27 |
| Nitrogen | 0.20 | 0.20 | 0.20 | 0.20 | | 0.04 | 0.00 | 0.17 |
| Ethane | 1.39 | 1.36 | 1.36 | 1.36 | | | | |
| Propane | 0.12 | 0.12 | 0.12 | 0.12 | | | | |
| Butane | 0.04 | 0.04 | 0.04 | 0.04 | | | | |
| Pentane | 0.04 | 0.04 | 0.04 | 0.04 | | | | |
| Methanol | | 0.01 | 0.01 | 0.01 | | | 75.01 | 0.48 |

| Stream | 38 | 42 | 44 | 48 | 54 | 60 | 68 | 70 |
|---|---|---|---|---|---|---|---|---|
| Pressure (bara) | 30.0 | 30.0 | 25.0 | 21.0 | 19.0 | 18.0 | 40.0 | 77.0 |
| Temp (° C.) | 250 | 650 | 883 | 203 | 250 | 40 | 70 | 70 |
| Flow (kmol/h) | 7946 | 6530 | 22640 | 30369 | 21755 | 21646 | 7764 | 3488 |
| Mole fraction (%) | | | | | | | | |
| Water | 100.00 | | 32.27 | 19.17 | | 0.25 | 0.21 | 0.15 |
| Hydrogen | | | 32.7 | 53.52 | 74.71 | 74.33 | 94.93 | 59.60 |
| Carbon Monoxide | | | 6.53 | 0.18 | 0.25 | | 0.88 | 5.58 |
| Carbon Dioxide | | | 5.09 | 9.20 | | | 1.94 | 2.13 |
| Methane | | | 0.50 | 0.88 | 1.23 | 1.48 | 1.97 | 32.10 |
| Nitrogen | | 79.00 | 22.90 | 17.06 | 23.82 | 23.94 | 0.07 | 0.41 |
| Oxygen | | 21.00 | | 0.00 | | | | |
| Methanol | | | | | | | 0.00 | 0.03 |

The invention claimed is:

1. A process for the co-production of methanol and ammonia comprising the steps of: (a) forming a first synthesis gas stream by reacting a first portion of a hydrocarbon feedstock and steam in a steam reformer, (b) forming a second synthesis gas stream in parallel to the first synthesis gas stream by reacting a second portion of the hydrocarbon feedstock with an oxygen-containing gas and steam in an autothermal reformer, (c) synthesising methanol from a first process gas comprising the first synthesis gas stream, and (d) synthesising ammonia from a second process gas prepared from the second synthesis gas stream, wherein a purge stream containing hydrogen is recovered from the methanol synthesis step (c), the purge gas stream containing hydrogen is separated into a hydrogen-rich gas stream and a hydrogen-depleted gas stream, the hydrogen-rich gas stream is combined with the second synthesis gas stream, and the hydrogen-depleted gas is fed to the autothermal reformer.

2. A process according to claim 1 wherein the hydrocarbon feedstock is natural gas.

3. A process according to claim 1 where the hydrocarbon feedstock is desulphurised and then divided into the first portion and the second portion.

4. A process according to claim 1 wherein one or more process streams selected from the hydrocarbon feedstock, steam and oxygen-containing gas are preheated in a flue gas duct of the steam reformer.

5. A process according to claim 1 wherein the oxygen containing gas is selected from air or an oxygen-enriched air.

6. A process according to claim 1 wherein the autothermal reformer is operated at a pressure in the range 80 to 200 bar abs.

7. A process according to claim 1 wherein the methanol synthesis step is operated at a pressure equal or greater than the operating pressure of the autothermal reformer.

8. A process according to claim 1 wherein the methanol is synthesised in a methanol production unit by steps comprising passing the first process gas through a bed of methanol synthesis catalyst disposed in a methanol synthesis reactor to form a methanol-containing product gas, recovering methanol and an unreacted gas stream from the methanol-containing product gas, returning a portion of the unreacted gas stream to the methanol synthesis reactor in a synthesis loop and recovering the purge stream containing hydrogen from the synthesis loop.

9. A process according to claim 1 wherein at least a portion of the synthesised methanol is purified by distillation.

10. A process according to claim 1 wherein at least a portion of the methanol is reacted with air over an oxidation catalyst in a formaldehyde production unit to form formaldehyde.

11. A process according to claim 1 wherein the second process gas is prepared by steps comprising passing the second synthesis gas through one or more stages of water-gas shift to form a shifted gas stream, separating carbon dioxide from the shifted gas stream in a carbon dioxide removal unit and converting any remaining carbon oxides present in the second process stream to methane in a methanation unit downstream of the carbon dioxide removal unit.

12. A process according to claim 1 wherein the ammonia is synthesised in an ammonia production unit by passing the second process gas through a bed of ammonia synthesis catalyst disposed in an ammonia synthesis reactor to form an ammonia-containing product gas, recovering ammonia and an unreacted gas stream from the ammonia-containing product gas, returning a portion of the unreacted gas stream to the ammonia synthesis reactor in a synthesis loop and recovering a purge stream containing methane from the synthesis loop.

13. A process according to claim 1 wherein at least a portion of the ammonia is reacted with carbon dioxide in a urea production unit to from urea.

14. A process according to claim 13 wherein at least a portion of the carbon dioxide is recovered from the purge gas stream recovered from the methanol loop.

15. A process according to claim 10 wherein at least a portion of the ammonia is reacted with carbon dioxide in a urea production unit to from urea, at least a portion of the formaldehyde is reacted with the urea to form a urea-formaldehyde concentrate, and at least a portion of the urea-formaldehyde concentrate is reacted with urea to form a stabilised urea product.

* * * * *